United States Patent
Ibrahim et al.

(10) Patent No.: US 7,118,732 B2
(45) Date of Patent: Oct. 10, 2006

(54) TOOTH-WHITENING COMPOSITIONS COMPRISING SILICONE POLYMER AND METHODS THEREFOR

(75) Inventors: Sayed Ibrahim, Somerset, NJ (US); Prithwiraj Maitra, Somerset, NJ (US); Suman K. Chopra, Dayton, NJ (US); Eugene Pashkovski, Bridgewater, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/842,154

(22) Filed: May 10, 2004

(65) Prior Publication Data

US 2005/0287084 A1 Dec. 29, 2005

(51) Int. Cl.
*A61Q 11/00* (2006.01)
(52) U.S. Cl. .......................................... 424/49; 424/57
(58) Field of Classification Search ................ 424/49, 424/57
See application file for complete search history.

(56) References Cited

U.S. PATENT DOCUMENTS

| | | | | |
|---|---|---|---|---|
| 4,177,258 | A * | 12/1979 | Gaffar et al. ................ 424/52 |
| 4,758,646 | A | 7/1988 | Raleigh et al. |
| 5,188,822 | A * | 2/1993 | Viccaro et al. ............... 424/52 |
| 5,397,848 | A | 3/1995 | Yang et al. |
| 5,427,770 | A * | 6/1995 | Viccaro et al. ............... 424/54 |
| 5,827,505 | A | 10/1998 | Hughes et al. |
| 6,139,823 | A | 10/2000 | Drechsler et al. |
| 6,165,510 | A * | 12/2000 | Baines et al. ................ 424/489 |
| 6,193,958 | B1 * | 2/2001 | Edwards et al. ............... 424/49 |
| 6,210,690 | B1 * | 4/2001 | Nabeshima et al. ........ 424/401 |
| 6,294,154 | B1 * | 9/2001 | Hughes ........................ 424/49 |
| 6,403,074 | B1 | 6/2002 | Blankenburg et al. |
| 6,485,716 | B1 | 11/2002 | Fei et al. |
| 6,503,484 | B1 * | 1/2003 | Littlewood et al. ........... 424/52 |
| 6,596,298 | B1 | 7/2003 | Leung et al. |
| 6,613,812 | B1 | 9/2003 | Bui et al. |
| 6,669,930 | B1 * | 12/2003 | Hoic et al. ..................... 424/49 |
| 2002/0142014 | A1 * | 10/2002 | Afriat et al. ................. 424/401 |

FOREIGN PATENT DOCUMENTS

| | | |
|---|---|---|
| EP | 0 371 551 A2 | 6/1990 |
| EP | 1 216 681 A2 | 12/2001 |
| EP | 1207843 | 5/2002 |
| KR | 2002 021 446 A | 3/2002 |
| WO | 01/01940 * | 1/2001 |
| WO | WO 01/01939 A1 | 1/2001 |
| WO | WO 01/13884 A3 | 3/2001 |
| WO | WO 2005/016298 A2 | 2/2005 |

OTHER PUBLICATIONS

English language translation WO 01/13884, Mar. 2001.*
Banfield, et al., *Aggregation-Based Crystal Growth and Microstructure Development in Natural Iron Oxyhydroxide Biomineralization Products*, Science, vol. 289, pp. 751-754, (2000).
Niwa M. et al. "Polishing and Whitening Properties of Toothpaste Containing Hydroxyapatite". *Journal of Materials Science—Materials in Medicine* vol. 12, No. 3, Mar. 2001. pp. 277-281.

* cited by examiner

*Primary Examiner*—Margaret G. Moore
(74) *Attorney, Agent, or Firm*—Michael F. Morgan

(57) ABSTRACT

Tooth-imparting whiteness to fluids comprising a particulate whiteness-imparting particles such as hydroxyapatite and an organosiloxane polymer are disclosed. Methods of use of the fluids are also disclosed.

2 Claims, No Drawings

TOOTH-WHITENING COMPOSITIONS COMPRISING SILICONE POLYMER AND METHODS THEREFOR

FIELD

This invention relates to compositions and methods for imparting whiteness to teeth.

BACKGROUND

Consumers wishing to whiten their teeth have a limited variety of products from which to choose. Successful application of some products, such as veneers, crowns and caps, involves destruction of tooth enamel, and requires the services of a dental professional such as a dentist. Thus, there is an ongoing need for new compositions and methods for imparting whiteness teeth, in particular compositions and methods for whitening teeth that do not necessitate the destruction of tooth enamel.

SUMMARY

Accordingly, the present inventors have succeeded in developing compositions and methods for imparting whiteness to teeth. The compositions can be tooth-coating fluids comprising particles which are white in color, such as particles comprising a hydroxyapatite, and at least one organosiloxane polymer such as a film-forming hydrophilic anionic organosiloxane polymer, for example, a dimethicone/acrylate copolymer or a dimethicone copolyol. Application of the compositions to the teeth in a mammal such as, for example, a human, coats the teeth and imparts a whiteness to the teeth.

Thus, in various embodiments, the present invention can involve a tooth-coating fluid. The tooth-coating fluid can comprise a plurality of white particles and at least one organosiloxane polymer.

Methods of imparting whiteness to a tooth in a mammal are also encompassed in various embodiments of the present invention. The methods can comprise applying to the tooth a whiteness-imparting amount of a fluid comprising a plurality of white particles and at least one organosiloxane polymer.

Methods of making a tooth-coating fluid are also encompassed in various embodiments of the present invention. The methods can comprise mixing a plurality of white particles with at least one organosiloxane polymer.

In various embodiments, the organosiloxane polymer can be a film-forming hydrophilic anionic organosiloxane polymer, for example, a copolymer comprising subunits of a dimethicone copolyol and a polyoxyalkylene ether, in particular a dimethicone/acrylate copolymer. The dimethicone/acrylate copolymer can comprise t-butyl acrylate, methacrylic acid and dimethicone copolyol such as the copolymer having a Chemical Abstract Service designation of CAS No. 248935-80-0. The copolymer can have a weight average molecular weight, a number average molecular weight, a Z-average molecular weight or a viscosity average molecular weight of from at least about 1,000 to about 1,000,000, or from at least about 75,000 to about 100,000.

In various embodiments, the organosiloxane polymer can be a silicone copolyol such as a dimethicone copolyol. In these embodiments, a copolyol can comprise a siloxane-oxyalkylene copolymer, such as a dimethicone copolyol disclosed in U.S. Pat. No. 6,485,716 B1 to Fei et al. The copolyol can have a weight average molecular weight, a number average molecular weight, a Z-average molecular weight or a viscosity average molecular weight of from at least about 1,000 to about 1,000,000, or from at least about 75,000 to about 100,000.

In various embodiments, the plurality of white particles can be independently comprised of a material selected from the group consisting of a calcium phosphate, a titanium oxide, an aluminum oxide, a tin oxide, a calcium oxide, a magnesium oxide, a polyethylene, a polypropylene, a ethylene/propylene copolymer, a polytetrafluoroethylene, a polyhexafluoropropene and combinations thereof.

The plurality of white particles can comprise a calcium phosphate, such as a hydroxyapatite, in particular a crystalline hydroxyapatite. The average diameter of such particles can be from about 0.5 microns to about 500 microns, from about 10 microns to about 100 microns, or from about 20 microns to about 50 microns.

DETAILED DESCRIPTION

In various embodiments, the present invention provides a tooth-coating fluid comprising a whiteness-imparting particles and a hydrophilic organosiloxane polymer, such as a hydrophilic silicone polymer. The whiteness-imparting particles can comprise a white particle or aggregate particles. In some configurations, the white particles can be opaque particles.

In various embodiments, tooth-coating compositions disclosed herein can comprise a fluid carrier. The compositions can comprise a calcium phosphate, and an organosiloxane polymer. "Fluid," as used herein, means a non-gaseous, non-solid substance such as, for example, a liquid or a semi-solid. The viscosity of a fluid can range from that of a freely flowable, low viscosity fluid, to that of an extremely high viscosity fluid. An extremely high viscosity fluid can be a fluid in which flow can appear slow or imperceptible to a human observer under ambient conditions. The term "fluid" as used herein is also intended to include thixotropic liquids, gels, colloids, pastes, ointments, and gums. A fluid of the present invention can have a dynamic viscosity, measured at 25° C., ranging from at least about 0.18 milliPascal-sec (mPa-s), at least about 0.5 mPa-s, at least about 1 mPa-s, at least about about 2 mPa-s, at least about 50 mPa-s, at least about 100 mPa-s, at least about 10 mPa-s, at least about 100 mPa-s up to about 100,000 mPa-s, up to about 1,000,000 mPa-s, up to about 10,000,000 mPa-s, or up to about 100,000,000 mPa-s. Without being limited by theory, it is believed that the viscosity of a fluid herein will vary with the amount (percentage) of a film-forming polymer component and the weight average molecular weight of a film-forming polymer component.

In various embodiments, the whiteness-imparting particles can be any white colored or white pigmented particles such as, for example, white mineral particles, white metal oxide particles, or a white polymer particles. As used herein, "white" is considered a color, and a "white" color can be any color commonly perceived as white, for example colors set forth in the Vita Shade Guide scale of whiteness, or colors that are perceived as whiter than those displayed in the Vita Shade Guide. In some embodiments, white mineral particles can comprise a non-toxic mineral or salt that can impart a white color. In various embodiments, the white particles can comprise a calcium phosphate. In various configurations, the calcium phosphate can have a structure selected from tetra-calcium phosphate, amorphous calcium phosphate, alpha-tricalcium phosphate, beta-tricalcium phosphate and hydroxyapatite ($Ca_{10}(PO_4)_6(OH)_2$). The calcium phosphate in various embodiments, can be a substantially aqueous insoluble calcium phosphate and non-crystalline, poorly crystalline or crystalline form such as, for example, crystalline hydroxyapatite. A hydroxyapatite can be, in some configurations, an aggregate of hydroxyapatite particles such as nano-HAP (BASF corporation; Banfield et al., Science 289, 751–754, 2000). Non-limiting examples of a hydroxyapatite include Hydroxyapatite A1 (Himed, Old Bethpage, N.Y.), and a hydroxyapatite supplied by BASF corporation. In some configurations, hydroxyapatite particles can comprise aggregates of smaller hydroxyapatite particles. In non-limiting example, such aggregates can have a mean diameter of from about 100 nm to about 1000 nm, and comprise hydroxyapatite particles having a mean diameter of from about 0.1 nm to about 10 nm.

The whiteness-imparting particles can be, in some configurations, a metal oxide. The metal oxide can comprise any metal oxide that provides a white color, such as, for example, titanium oxide, aluminum oxide, tin oxide, calcium oxide, magnesium oxide, barium oxide, or a combination thereof.

The whiteness-imparting particles can be, in some configurations, polymeric white-colored particles such as disclosed in U.S. Pat. No. 6,669,930 to Hoic. Polymeric white-colored particles can comprise, in non-limiting example, polyethylene (PE), polypropylene, ethylene/propylene copolymer, polytetrafluoroethylene (PTFE) or polyhexafluoropropene. In non-limiting example, the polymeric white-colored particles can be polyethylene PE220, polypropylene, or PTFE as supplied by PreSperse, Inc., Somerset N.J. In non-limiting example, the polymeric whiteness-imparting particles can comprise a polymer having a weight average molecular weight, a number average molecular weight, a Z-average molecular weight or a viscosity average molecular weight ranging from about 100 to about 10,000,000; from about 200 to about 5,000,000; from about 500 to about 1,000,000; from about 1,000 to about 500,000; from about 10,000 to about 100,000, or from about 20,000 to about 50,000.

In some embodiments, the whiteness-imparting particles can comprise pearlescent particles. In some configurations, the pearlescent particles can provide a white pearlescent appearance to a composition herein. "Pearlescence" and "pearlescent," as used herein, refers to an optical property of a material in which the material can have a pearl-like, lustrous appearance. In some configurations, a pearlescent material can provide an appearance of depth. In some aspects, a pearlescent material can further provide an appearance of shine. Without being limited by theory, pearlescent particles are believed to partially reflect and partially refract incident light. The extent of partial refraction or reflection of incident light by a pearlescent material can depend on the angle of light incidence and/or the angle of viewing. Pearlescent particles used in the compositions described herein can provide aesthetic or cosmetic effects such as, for example, sparkle or luster.

Pearlescent particles can comprise a single mineral or chemical species, such as, for example a silicate such as mica, or bismuth oxychloride. By "mica" is meant any one of a group of hydrous aluminum silicate minerals with platy morphology and perfect basal (micaceous) cleavage. Mica can be, for example, sheet mica, scrap mica or flake mica, as exemplified by muscovite, biotite or phlogopite type micas. In some embodiments, the pearlescent particles can comprise a complex comprising more than one mineral or chemical species, such as, for example, mica coated with a metal oxide such as titanium oxide. Pearlescent particles can also be of biological origin, for example fish scale or mother-of-pearl. Certain pearlescent particles of biological origin can comprise calcium carbonate, such as, for example, pearl, mollusk shell such as mother-of-pearl obtained from oyster shell, or nacre.

In some embodiments, white pearlescent particles can be, for example, those described as Timiron® pigments, Biron® powders, Biron® dispersions or Nailsyn® dispersions (all registered trademarks of EM Industries, Inc. Hawthorne, N.Y., division of E. Merck). For example, mica titanium particles can be pearlescent particles such as Timiron® particles. White pearlescent mica titanium particles can be, for example "Silverwhite" Timiron® particles such as Timiron® Starluster MP-115, Timiron® Supersheen MP-1001, Timiron® Sparkle MP-47, Timiron® Supersilk MP-1005, Timiron® Pearl Flake MP-10, Timiron® Pearl Sheen MP-30, Timiron® Super Silver Fine, Timiron® Gleamer Flake MP-111, Timiron® Ultraluster MP-45, Timiron® Transwhite MP-18, Timiron® Diamond Cluster MP-149, Timiron® Super Silver, Timiron® Stardust MP-80, Timiron® Arctic Silver or Timiron® Snowflake MP-99.

A tooth-coating fluid of the present invention can comprise white particles from about 0.01% (w/w) up to about 50% (w/w), from about 0.1% (w/w) up to about 20% (w/w), from about 1% (w/w) up to about 19% (w/w), from about 2% (w/w) up to about 18% (w/w), from about 3% (w/w) up to about 17% (w/w), from about 4% (w/w) up to about 16% (w/w), or from about 6% (w/w) up to about 15% (w/w). In some configurations, the white particles (including pearlescent particles) can have an average size of from about 0.01 micron to about 500 microns, from about 0.5 micron to about 100 microns, or from about 2 microns to about 20 microns in diameter or longest dimension. Such particles as referenced herein are intended to include primary particles as well as aggregates of particles.

In various embodiments of the present invention, a polymer comprised by a fluid of the present invention can be a hydrophilic polymer. A hydrophilic polymer, as used herein, means a polymer having a solubility in water of at least about 1 gram polymer per 100 grams water at ambient temperature. In various embodiments, a polymer comprised by a fluid of the present invention can be a film-forming polymer. In various aspects, the polymer can be a polymeric binder that can promote adhesion between white particles and teeth to which the fluid is applied. In various aspects, the polymer can be an adhesive that can bind both to teeth and to the white particles. In various aspects, the polymer can be a surfactant. In some embodiments, a surfactant polymer of the present invention can reduce the surface tension between white particles comprising the fluid present invention, and teeth to which the fluid is applied. In some embodiments, a surfactant polymer of the present invention can reduce the surface tension between white particles comprising a fluid of the present invention, and an aqueous liquid such as saliva comprised by an oral cavity. In some aspects, the polymer can act as a wetting agent for the white particles. In some aspects, a surfactant polymer encompassed by the present invention can have detergent properties.

In various embodiments of the present invention, a polymer comprised by a fluid of the present invention can be an organosiloxane polymer The organosiloxane polymer can be generally characterized as follows:

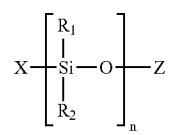

wherein $R_1$ and $R_2$ are independently, organic radical groups such as alkyl, aryl, or alkoxy radicals having from 1 to about 40 carbons; n is an integer from 1 to about 200; X and Z can comprise organic substituents, one or both of which confer hydrophilicity to the polymer. In some embodiments, $R_1$ and $R_2$ can be the same organic radical groups.

The hydrophilic organosiloxane polymer can also be an anionic organosiloxane polymer such as is described in European Patent EP1207843 to Engesser, which is hereby incorporated by reference in its entirety. The anionic organosiloxane polymer can comprise a PEG/PPG conjugate of a dimethicone/acrylate copolymer, and can be a polymer of the following structure:

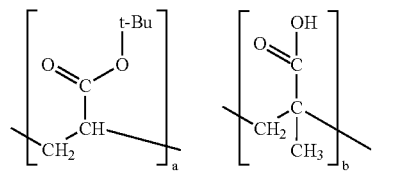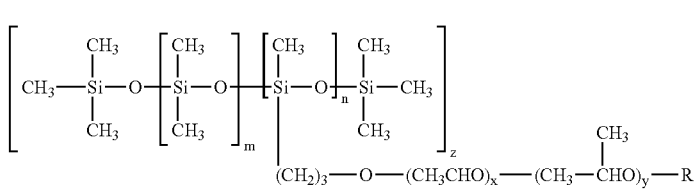

wherein a, b, m, n, x, y and z each represent a positive integer ranging from 1 up to about 100,000. The dimethicone/acrylate copolymer as shown above, is the polymerized reaction product of t-butyl acrylate, methacrylic acid and dimethicone copolyol. The copolymer has an International Nomenclature of Cosmetic Ingredients (INCI) designation of PEG/PPG-25/25 Dimethicone/Acrylates Copolymer, and a Chemical Abstracts Service Registry Number (CAS No.) of 248935-80-0. The copolymer can be, for example, the copolymer comprised by Luviflex Silk® (BASF).

The hydrophilic organosiloxane polymer can also be, in various embodiments, a film-forming organosiloxane polymer.

A hydrophilic organosiloxane polymer can be prepared by a number of procedures known in the art. For example, one procedure can comprise subjecting ethyleneically unsaturated monomers to free-radical polymerization in the presence of polyalkylene oxide-containing silicone derivatives, as described in U.S. Pat. No. 6,403,074, which is incorporated in its entirety by reference. Another method known in the art can involve introducing a hydrophilic component including a hydrophilic portion and a silicone polymer portion into a silicone polymeric material, as described in U.S. Pat. No. 5,397,848, which is incorporated in its entirety by reference. Yet another method known in the art involves esterifying an alpha-beta unsaturated polyether produced by polymerizing alkylene oxide, in the presence of ally alcohol with an alpha-beta unsaturated organic acid, and subsequently performing an addition reaction between a terminal unsaturation and a SiH compound in the presence of a platinum catalyst, as described in U.S. Pat. No. 4,758,646, which is incorporated in its entirety by reference.

The organosiloxane polymer can also be, in various embodiments, a silicone copolyol such as a dimethicone copolyol, for example a dimethicone copolyol described in U.S. Pat. No. 6,485,716 to Fei et al., which is hereby incorporated by reference in it entirety. Some of these silicone copolyols include copolyols which may be represented by Formula I or Formula II, as follows.

In certain embodiments, a silicone copolyol of Formula I can have the following structure:

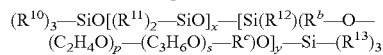

wherein each of $R^{10}$, $R^{11}$, $R^{12}$ and $R^{13}$ may be the same or different and each is selected from the group consisting of C1–C6 alkyl; $R^b$ is the radical $-C_mH_{2m}-$; $R_c$ is a terminating radical which can be hydrogen, an alkyl group of one to six carbon atoms, an ester group such as acyl, or an aryl group such as phenyl; m is from two to about eight; p and s have values such that the oxyalkylene segment $-(C_2H_4O)_p-(C_3H_6O)_s-$ has a molecular weight in the range of 200 to 5,000, wherein the segment can comprise, in certain configurations, from about fifty up to one hundred mole percent of oxyethylene units $-(C_2H_4O)_p-$ and from about one up to about fifty mole percent of oxypropylene units $-(C_3H_6O)_s-$; x has a value of about 8 to about 400; and y has a value of from about 2 to about 40. In some configurations, each of $R^{10}$, $R^{11}$, $R^{12}$ and $R^{13}$ can be a methyl group; $R^c$ can be H; m can be three or four, the group $R^b$ can be the radical $-(CH_2)_3-$; and the values of p and s can be such as to provide a molecular weight of the oxyalkylene segment $-(C_2H_4O)_p-(C_3H_6O)_s-$ of between about 1,000 to about 3,000. In certain configurations, p and s can each have a value of from about 18 to about 28.

In certain embodiments, a silicone copolyol of Formula II can have the following structure:

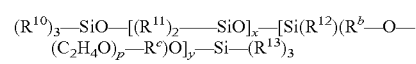

wherein p has a value of from about 6 to about 16; x has a value of from about 6 to about 100; and y has a value of 1 to about 20 and the other moieties have the same definition as defined in Formula I.

In certain embodiments, in both Formulas I and II shown above, the siloxane-oxyalkylene copolymers can take the form of endblocked polyethers in which the linking group $R^b$, the oxyalkylene segments, and the terminating radical $R^c$ occupy positions bonded to the ends of the siloxane chain. Thus, one or more of the $R^{10}$, $R^{11}$, $R^{12}$ and $R^{13}$ substituents which are attached to the two terminal silicon atoms at the end of the siloxane chain can be substituted with the segment $-R^b-O-(C_2H_4O)_p-(C_3H_6O)_s-R^c$ or with the segment $-R^b-O-(C_2H_4O)_p-R^c$. In some configurations, a siloxane chain can comprise moieties such as $-R^b-O-(C_2H_4O)_p-(C_3H_6O)_s-R^c$ or the segment $-R^b-O-(C_2H_4O)_p-R^c$. These moieties can at either end and/or internal to a siloxane chain.

A dimethicone copolyol utilized in various embodiments of the present invention can be a commercially available dimethicone copolymer, such as, for example a copolymer available from a commercial supplier such as Dow Corning Corporation, Midland, Mich.; General Electric Company, Waterford, N.Y.; Witco Corp., Greenwich, Conn.; and Goldschmidt Chemical Corporation, Hopewell, Va. Non-limiting examples of some dimethicone copolyols include DOW CORNING® 5225C from Dow Corning which is a 10% dimethicone copolyol in cyclomethicone; DOW CORNING® 2-5185C® which is a 45–49% dimethicone copolyol in cyclomethicone; and SILWET L-7622 from Witco; ABIL EM97 from Goldschmidt which is a 85% dimethicone copolyol in D5 cyclomethicone.

In various embodiments, the total polymer concentration of a fluid of the present invention can be at least about 0.1% (w/w) up to about 99% (w/w), from at least about 1% (w/w) up to about 90% (w/w), from at least about 1% (w/w) up to about 94.9% (w/w), from at least about 10% (w/w) to about 80% (w/w), or from at least about 20% (w/w) to about 70% (w/w). In some configurations, the polymer can have a weight average molecular weight, a number average molecular weight, a Z-average molecular weight or a viscosity average molecular weight of from about 100 to about 10,000,000; from about 500 to about 5,000,000; from about 1,000 to about 1,000,000; from about 5,000 to about 500,000; from about 10,000 to about 250,000, or from about 75,000 to about 100,000.

In various embodiments, a tooth-coating composition as described herein can further comprise calcium chloride ($CaCl_2$). Without being limited by theory, calcium chloride is believed to increase dispersion of other components of a tooth-coating composition, such as dispersion of hydroxyapatite particles. In some configurations, a tooth-coating composition can comprise from about 0.005% to about 10% $CaCl_2$.

In various embodiments, a tooth-coating composition as described herein can be adhesive towards teeth. Without being limited by theory, it is believed that the adhesiveness of a fluid herein will vary with the amount (percentage) of a film-forming polymer component and the weight average molecular weight of a film-forming polymer component.

In various embodiments, a tooth-coating fluid of the invention can form a film on a tooth surface following its application thereon. In certain embodiments, a formulation of a tooth-coating fluid of the present invention can comprise white particles, a film-forming polymer and at least one solvent. The solvent can be, in certain aspects, a polymer-dissolving solvent. The solvent can be, in some configurations, a volatile solvent. In various embodiments, the solvent can be an organic solvent, such as, for example, an alcohol, such as ethanol. In certain aspects, the organic solvent can be a water-miscible solvent. In certain aspects, the organic solvent can have surfactant activity, such as detergent activity. A composition can comprise a solvent in an amount of from about 1% (w/w) to about 90% (w/w), from about 5% (w/w) to about 98.9% (w/w), from about 10% (w/w) to about 80% (w/w), from about 20% (w/w) to about 70% (w/w), or from about 30% (w/w) to about 60% (w/w).

In some embodiments of the present invention, a film can form from a tooth-coating fluid as the solvent is removed, for example through evaporation. In some embodiments, a film can form as monomers comprised by the composition polymerize. Without being limited by theory, it is believed that the longevity of a film formed from a composition herein on teeth in an oral cavity varies with the amount (percentage) of a film-forming polymer component in the composition and the weight average molecular weight of a film-forming polymer component.

In various embodiments, a tooth-coating composition as described herein can be an adhesive that adheres to teeth. Without being limited by theory, it is believed that the adhesiveness of the fluid of the present invention will vary with the amount (percentage) of the film-forming organosiloxane polymer component and the weight average molecular weight of the film-forming organosiloxane polymer component. Adhesiveness can be measured using standard adhesion tests known in the art, for example, the adhesive test disclosed in U.S. Pat. No. 6,613,812 to Bui. In certain embodiments, the adhesiveness between a tooth and a film formed from a fluid of the present invention can be from about at least 500 pounds per square inch (PSI), at least 1,000 PSI, at least 2,000 PSI, or greater.

In various embodiments, a tooth-coating fluid of the present invention can comprise, in addition to white particles and a film-forming polymer such as a silicone polymer, at least one non-silicone polymer. In various configurations, non-limiting examples of non-silicone polymers that can be comprised by a tooth-coating fluid of the present invention include a cellulose such as carboxymethylcellulose acetate butyrate, cellulose acetate butyrate, or ethyl cellulose, and a polyvinylpyrrolidone/vinyl acetate copolymer such as Luviskol® 37E (BASF).

In various embodiments, a tooth-coating fluid of the present invention can comprise, in addition to white particles and a film-forming polymer, a fumed silica such as, for example, Cab-O-Sil® MS 55 (Cabot Corp.). In addition, a tooth-coating fluid of the present invention can further comprise a cocamidopropyl betaine such as for example, Tego Betaine® L-7.

In various embodiments, a tooth-coating composition of the present invention can further comprise, in addition to or instead of white particles, a non-white colorant or pigment. The term "colorant" is used herein to describe a substance that can impart a color when applied to a tooth. A color, as used herein, can be any perceivable hue, tint, or shade, including but not limited to spectrum colors, colors comprised within the L*a*b* color space, colors comprised within the RGB color space, as well as black, brown, gray and white. In various embodiments, the colorant can be a pigment or dye.

In some configurations, the colorant can comprise a plurality of pigment particles. A pigment, as used herein, can mean a particulate colorant. In some configurations, the compositions of the present invention can comprise one or more colorants at a concentration, individually or in total, of from about 0.1% (w/w) up to about 20% (w/w), from about 1% (w/w) up to about 19% (w/w), from about 2% (w/w) up to about 18% (w/w), from about 3% (w/w) up to about 17% (w/w), from about 4% (w/w) up to about 16% (w/w), or from about 6% (w/w) up to about 15% (w/w). In some configurations, the pigment particles can have an average size of from about 0.01 micron to about 1000 microns, from about 0.2 micron to about 500 micron, from about 0.3 micron to about 100 microns, or from about 0.5 microns to about 50 microns in diameter or longest dimension.

In certain embodiments, the non-white colorant can be a colorant approved for incorporation into a food, drug or cosmetic by a regulatory agency, such as, for example, FD&C or D&C pigments and dyes approved by the FDA for use in the United States. Non-limiting examples of non-white colorants include FD&C Red No. 3 (sodium salt of tetraiodofluorescein), Food Red 17, 6-hydroxy-5-{(2-methoxy-5-methyl-4-sulphophenyl)azo}-2-naphthalenesulfonic acid, Food Yellow 13, mono sulphonic acid of quinophtalone, disulphonic acid of quinophtalone, monosulphonic acid of 2-(2-quinolyl) indanedione, disulphonic acid of 2-(2-quinolyl) indanedione, FD&C Yellow No. 5, FD&C Yellow No. 6, FD&C Green No. 3, FD&C Blue No. 1, FD&C Blue No. 2, D&C Red #30, phthalocyanine green, salts thereof and mixtures thereof.

In some embodiments, the non-white colorant can be a dye lake pigment. In some configurations, the dye lake can be a calcium or aluminum salt of an FD&C dye such as, for example, FD&C Green #1 lake, FD&C Blue #2 lake, D&C Red #30 lake or FD&C Yellow #15 lake, or mixtures thereof.

In various embodiments, the non-white colorant can comprise an inorganic pigment. Non-limiting examples of inorganic pigments can include certain metal oxide pigments such as for example, copper oxide, iron oxide and chromium oxide. Other non-white inorganic pigments that can be comprised by a tooth-coating fluid alone or in combination can be, for example, mineral pigments, such as ultramarine blue (lapis lazuli).

In certain configurations, the colorant can comprise a dye contained within a water-insoluble polymer. In non-limiting example, the dye FD&C Blue #1 can be contained within a water-insoluble polymer such as a polyethylene such as that found in polyethylene beads (e.g., Microblue Spectrabeads, Micropowders, Inc.) In certain embodiments, the colorant can be a non-bleeding dye.

In various embodiments, the tooth-coating composition of the present invention can further comprise a therapeutic active. In various embodiments, a therapeutic active can be selected from the group consisting of anti-caries agents, anti-sensitivity agents, anti-microbial agents, bleaching agents, and combinations thereof. In non-limiting example, a therapeutic active can be an agent set forth in U.S. Pat. No. 6,596,298 to Leung.

In various embodiments, the present invention provides methods for imparting whiteness to teeth in a mammal. The mammal can be a human mammal. The methods can comprise applying to a mammal's teeth a tooth-whitening amount of a fluid comprising whiteness-imparting particles and an hydrophilic organosiloxane polymer. In some configurations, the hydrophilic organosiloxane polymer can be an anionic silicone polymer as described herein. In some configurations, the whiteness-imparting particles can be white particles, such as calcium phosphate particles. In some configurations, the whiteness-imparting particles can comprise a calcium phosphate such as hydroxyapatite. The whiteness-imparting particles can comprise, in some configurations, titanium oxide, mica titanium, or a white polymer as described herein.

In various embodiments, the application of a fluid of the invention to teeth can result in a perceivable increase in tooth whiteness. The whiteness of a tooth that has been coated with a tooth-coating composition of the invention can be determined visually by comparison with the Vita Shade Guide scale of whiteness (in which tooth color is measured on a scale of standard shades ranging from darkest to lightest of C4, A4, C3, B4, A3.5, B3, D3, A3, D4, C2, C1, A2, D2, B2, A1, and B1), or measured by a skilled artisan using a color measurement instrument such as a Minolta CR-321 chromometer. For example, teeth to which the fluid has been applied can exhibit an increase in Vita Shade Guide whiteness of at least one increment, for example, from A1 to B 1. In addition, the presence of white particles in a composition herein can result in teeth that are brighter than B1 on the Vita Shade Guide scale of whiteness.

Application of a fluid composition of the invention can be accomplished using methods known in the art. For example, an applicator such as a brush can be dipped in a tooth-coating fluid described herein, and the fluid can then be painted onto teeth. In addition to brush application, other non-limiting modes of application can comprise applying a rinse comprising a tooth-coating fluid of the invention, applying a semi-solid form of a tooth-coating fluid of the invention from a stick resembling a lipstick, applying a semi-solid form using a crayon-like stick, spraying on the fluid, dabbing on the fluid using a towelette, or transferring the fluid from an adhesive strip. Adherence of a fluid of the invention to teeth can be promoted by allowing the fluid to dry following application to the teeth. In some embodiments, a film forms as the fluid dries or a solvent component of the fluid evaporates. A film once formed can remain on the tooth for at least about one hour to about one year, from at least about one day to about six months, from at least about one week to about three months, or from at least about two weeks to about two months. In various embodiments, a film formed on teeth can be removed through friction, e.g., as provided by tooth brushing or mechanical scraping, or, in some embodiments, through application of a solvent, such as, for example, ethanol. In addition, in some configurations, application of a composition of the invention to a tooth can have a therapeutically beneficial effect, as the film formed on teeth can act as a barrier that can reduce or prevent contact between teeth and acids present in the oral cavity.

In various embodiments, application of a fluid of the present invention to teeth requires no special equipment or training; for example, the fluid can be self-applied by an individual user, or applied by an esthetician. In some configurations, prior to application to teeth, the targeted teeth can be cleaned, e.g., through brushing, to promote good adhesion between the composition and the teeth. Alternatively, a dental professional such as a dental hygienist or a dentist can clean the targeted teeth more thoroughly using professional equipment and methods prior to fluid application.

In various embodiments, solvent comprised by the fluid can be removed following its application to teeth, e.g., through evaporation. In some configurations, a tooth-coating composition that is expected to endure for an extended period, for example, for six months to a year after application, can be applied by a dental professional such as a dentist or a dental hygienist.

The skilled artisan can select a percentage amount and weight average molecular weight of a polymer of the present invention depending on the intended usage. For example, a user desiring to whiten his or her teeth for one evening can use a formulation comprising a low percentage of polymer and/or a low average molecular weight polymer, while a user desiring a tooth-coating that lasts several months can use a formulation comprising a high percentage of polymer and/or a high average molecular weight polymer.

In various embodiments, the present invention encompasses methods of making the tooth-coating fluids described herein. In various configurations, the methods comprise combining an organosiloxane polymer and white particles. For example, a hydrophilic silicone polymer can be combined with hydroxyapatite particles. These components can be mixed using methods well known to skilled artisans. In certain configurations, a tooth-coating fluid can be made by combining an organosiloxane polymer and white particles such as hydroxyapatite particles in an organic solvent such as ethanol. In some configurations, other components of a tooth-coating fluid can also be added, such as, for example, a cellulose and/or a therapeutic active.

Some compositions and methods described herein are illustrated by the following non-limiting examples.

EXAMPLES 1–4

These Example illustrate compositions containing Dow Corning® 5225C dimethicone copolyol.

In these examples, a fluid comprising a mixture of the following substances can be provided in the designated amounts (percent w/w), as shown in Table 1:

TABLE 1

| COMPONENT | Example 1 | Example 2 | Example 3 | Example 4 |
|---|---|---|---|---|
| Hydroxyapatite particles 20 micron mean particle diameter | 25.6 | 19.2 | 25 | 20 |
| Dow Corning ® 5225C copolyol | 19.2 | 26.9 | 66.5 | 27.2 |
| Polyvinylpyrrolidone/Vinyl acetate (Luviskol VA 37E ®)* | — | — | — | 2 |
| Carboxymethylcellulose acetate butyrate (CMCAB) | — | 3.5 | 7 | 2.3 |
| Cellulose Acetate Butyrate | 3.4 | — | — | — |
| Ethyl Cellulose | — | — | 1.5 | 1 |
| Fumed Silica | — | — | — | 0.5 |
| Ethanol | 51.8 | 50.4 | — | — |
| Tego Betaine (Cocamidopropyl Betaine; N-(carboxy methyl)-N, N-Dimethyl-3-[(1-Oxococonut) amino-1-Propanaminium Hydroxide Inner Salt) | — | — | — | 47 |
| TOTAL (percentage) | 100 | 100 | 100 | 100 |

*Luviskol VA 37E ® (BASF) comprises a mixture of approximately 50% ethanol and approximately 50% copolymer of vinylpyrrolidone and vinyl acetate. It has an INCI name of VP/VA Copolymer, and a CAS number of 25086-89-9.

The compositions of these examples can be made by dissolving the Dow Corning® 5225C copolyol polymer in ethanol followed by addition of the hydroxyapatite particles. The two components can be mixed in a high speed mixer until homogeneous dispersion is obtained, followed by addition of the remaining components.

EXAMPLES 5–9

These Examples illustrate compositions that comprise Luviflex® Silk.

In these examples, a fluid comprising a mixture of the substances shown in Table 3 can be provided in the designated amounts (percent w/w):

TABLE 3

| Component | Example 7 | Example 8 | Example 9 | Example 10 | Example 11 |
|---|---|---|---|---|---|
| Hydroxyapatite particles 20 micron mean particle diameter | 15 | 16.6 | 18 | 15 | 15 |
| Luviflex ® Silk* | 27 | 66.6 | 64 | 65 | 63 |
| Polyvinylpyrrolidone/Vinyl acetate (Luviskol VA 37E ®)** | 27 | — | 8 | 10 | 7 |
| Carboxymethylcellulose acetate butyrate (CMCAB) | — | — | 7 | 7 | 7 |
| Silicone Adhesive in Dimethicone | — | — | — | — | 7 |
| Ethyl Cellulose | — | — | 2 | 1 | — |
| Fumed Silica | 1 | — | 1 | 0.5 | 1 |
| Ethanol | 20 | 16.8 | — | — | — |
| Plastigel*** | 10 | — | — | — | — |
| Dimethicone | — | — | — | 0.5 | — |
| TOTAL (percentage) | 100 | 100 | 100 | 99 | 100 |

*Luviflex ® Silk (BASF) comprises approximately 50% INCI PEG/PPG-25/25 Dimethicone/Acrylates Copolymer and approximately 50% ethanol (abs.)
**Luviskol VA 37E ® (BASF) comprises a mixture of approximately 50% ethanol and approximately 50% nonionic film-forming copolymer of vinylpyrrolidone and vinyl acetate. It has an INCI name of VP/VA Copolymer, and a CAS number of 25086-89-9.
***Plastigel is a mixture of polyethylene gel in mineral oil. It is believed to reduce sedimentation, provide hydrophobicity, and improve rheology of a composition.

The compositions of these examples can be made by dissolving the Luviflex® Silk organosiloxane polymer in ethanol followed by addition of the hydroxyapatite particles. The two components can be mixed in a high speed mixer until homogeneous dispersion is obtained, followed by addition of the remaining components.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

All references cited in this specification are hereby incorporated by reference in their entirety. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:

1. The method of imparting whiteness to a tooth, comprising applying to the tooth a whiteness-imparting amount of a fluid comprising hydroxyapatite particles and at least one organosiloxane polymer wherein the polymer has a Chemical Abstracts Service Registry Number of 248935-80-0.

2. The method of imparting whiteness to a tooth, comprising applying to the tooth a whiteness-imparting amount of a fluid comprising hydroxyapatite particles and at least one organosiloxane polymer wherein the polymer is of the formula $$X-[SiR^1R^2-O-]_n-Z$$

wherein $R^1$ and $R^2$ is each independently an alkyl, aryl, or alkoxy group comprising from 1 to about 40 carbons;

n is an integer of 1 to 200; and

X and Z are each an organic substituent, one or both of which confers hydrophilicity to the polymer.

* * * * *